(12) United States Patent
Oechsel

(10) Patent No.: US 6,427,680 B1
(45) Date of Patent: Aug. 6, 2002

(54) NASAL APPLICATOR AND A DISPENSER DEVICE INCLUDING SUCH AN APPLICATOR

(75) Inventor: François Oechsel, Louviers (FR)

(73) Assignee: Valois S.A., Neubourg (FR)

( * ) Notice: Subject to any disclaimer, the term of this patent is extended or adjusted under 35 U.S.C. 154(b) by 0 days.

(21) Appl. No.: 09/446,012

(22) PCT Filed: Jun. 10, 1998

(86) PCT No.: PCT/FR98/01196

§ 371 (c)(1), (2), (4) Date: Dec. 16, 1999

(87) PCT Pub. No.: WO98/57690

PCT Pub. Date: Dec. 23, 1998

(30) Foreign Application Priority Data

Jun. 18, 1997 (FR) .......................................... 97 07585

(51) Int. Cl.[7] ............................................. A61M 11/00
(52) U.S. Cl. ........................ 128/200.14; 128/200.24; 128/203.12; 128/207.18
(58) Field of Search ........................... 222/153, 402.11, 222/402.13, 182, 542, 538, 562; 604/58, 77, 94.01, 257, 279, 316; 128/200.14, 200.24, 203.12, 203.15, 207.18

(56) References Cited

U.S. PATENT DOCUMENTS

| | | | | |
|---|---|---|---|---|
| 4,830,224 A | * | 5/1989 | Brison | ........................ 222/153 |
| 5,203,840 A | * | 4/1993 | Graf et al. | ................... 222/321 |
| 5,257,726 A | * | 11/1993 | Graf et al. | ................... 222/320 |
| 5,439,177 A | * | 8/1995 | Graf et al. | ................... 239/333 |
| 5,901,703 A | * | 5/1999 | Ohki et al. | ............. 128/203.12 |
| 5,944,222 A | * | 8/1999 | Fuchs et al. | ................... 222/82 |
| 5,989,217 A | * | 11/1999 | Ohki et al. | ................... 604/94 |
| 6,059,150 A | * | 5/2000 | Fuchs et al. | ............. 222/321.2 |
| 6,145,703 A | * | 11/2000 | Opperman | ................... 222/82 |

FOREIGN PATENT DOCUMENTS

| | | |
|---|---|---|
| EP | 170 198 | 2/1986 |
| FR | 1 257 220 | 7/1961 |
| FR | 2 739 294 | 4/1997 |

* cited by examiner

Primary Examiner—John G. Weiss
Assistant Examiner—Darwin P. Erezo
(74) Attorney, Agent, or Firm—Sughrue Mion, PLLC

(57) ABSTRACT

A nasal applicator suitable for co-operating with a head (100) of a nasal dispenser device for dispensing a fluid or powder substance into the nose, said head (100) being designed to be inserted at least in part into a nostril when the device is actuated, said nasal applicator being characterized in that said applicator (200) co-operates with the end (110) of the head (100), said applicator (200) being provided with a bearing piece (201) that extends substantially transversely to the direction in which the substance is dispensed, said bearing piece (201) being suitable for coming to bear under the nostril against the top lip of the user so as to define an insertion angle at which said head (100) is inserted into the nostril.

11 Claims, 2 Drawing Sheets

NASAL APPLICATOR AND A DISPENSER DEVICE INCLUDING SUCH AN APPLICATOR

Figure 1:
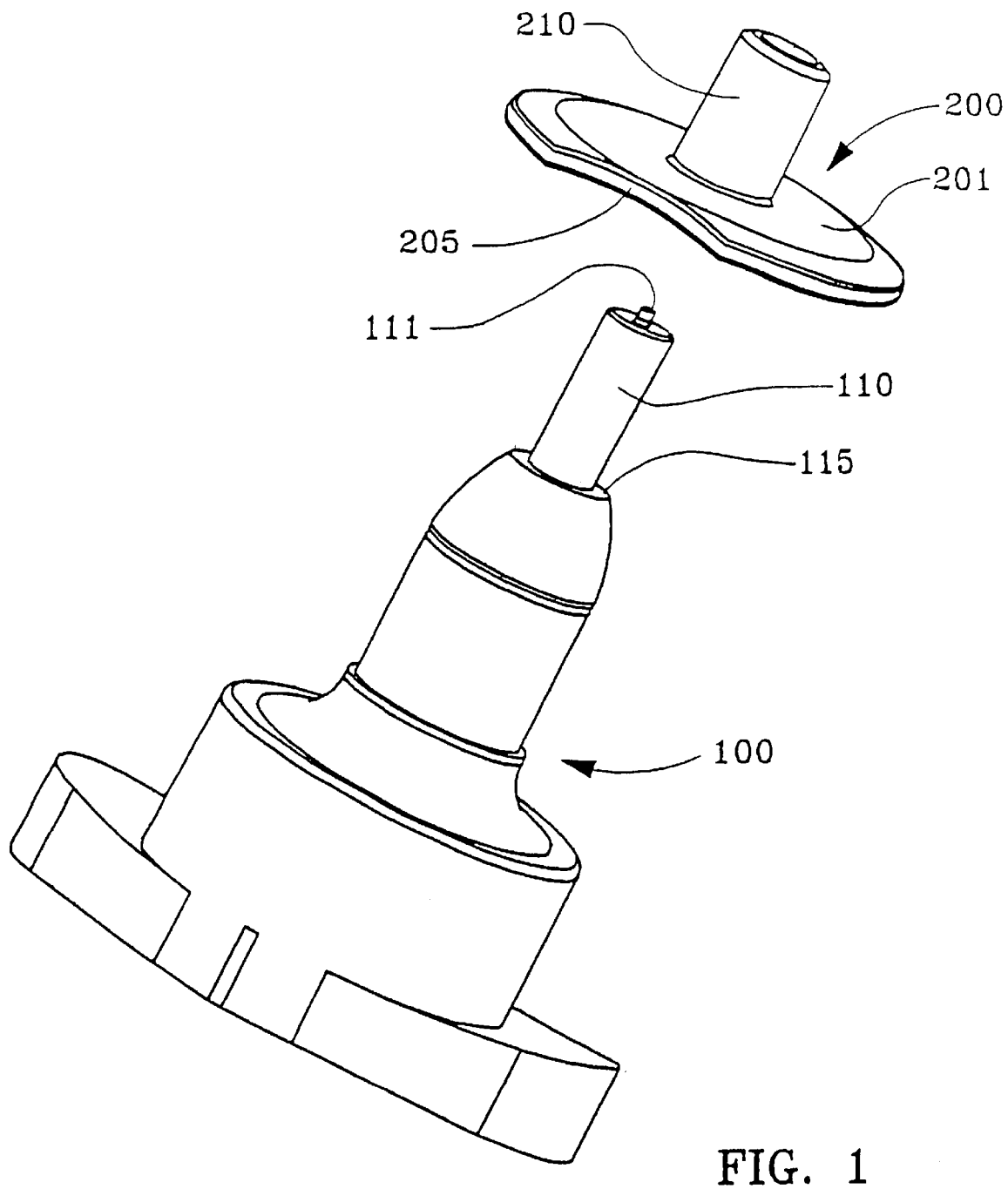
Figure 2:
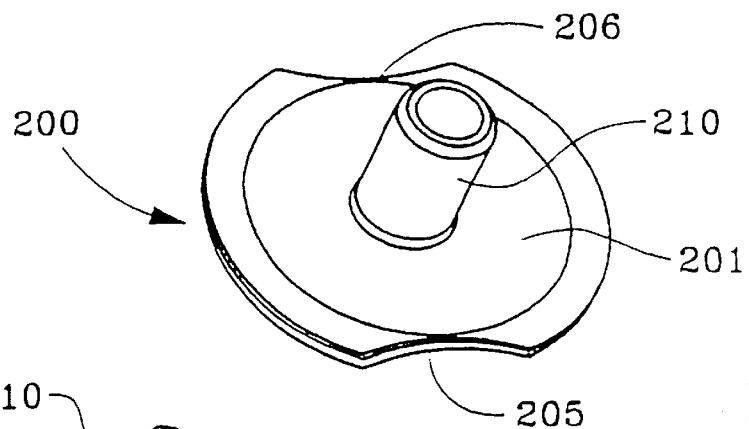

The present invention relates to a nasal applicator and to a dispenser device including such an applicator for dispensing a fluid or a powder substance into the nose. More particularly, the invention relates to an applicator of the type suitable for defining the direction in which the substance is dispensed into the nostril of the user.

Nasal dispenser devices are widespread in a variety of uses. Every one of such devices includes a head incorporating a substance-dispensing orifice, at least a portion of said head being designed to be inserted into the nostril of the user for the purpose of dispensing the substance. The user then actuates the device to expel a measured dose of substance into the nostril.

In certain uses, in particular in the field of pharmacy, the substances dispensed by nasal dispenser devices can be costly and/or must be measured out very accurately. It is therefore important to obtain the maximum effect from the dose of substance dispensed into the nostril each time the dispenser is actuated.

Currently, most nasal dispenser devices expel the dose of substance in a direction that is very substantially parallel to the nasal septum, towards the superior turbinate bone of the nostril.

Unfortunately, for certain substances, in particular in the field of pharmacy, the most effective portion for assimilating the substance is constituted by the inferior turbinate bone of the nostril.

In an attempt to solve that problem, some commercially-available dispensers are provided with pushers (or dispenser heads) that slope. Unfortunately, that type of sloping pusher is complicated and expensive to manufacture, in particular as regards molding. In addition, the effectiveness of such pushers is not guaranteed. Furthermore, the use of a sloping (or curved) pusher requires an expulsion channel that is quite long and prevents the use of internal nozzles. Internal nozzles offer many advantages. In particular, there is no danger of them becoming detached from the pusher (unlike external nozzles), and they make it possible to minimize effectively the unused volume inside the pusher.

Document FR-2 739 294 discloses such a sloping head. That document further discloses the use of a safety applicator designed to limit the portion of applicator penetrating into the nasal cavity to a predetermined length, in order to avoid any damaging contact between the applicator and the mucus membranes of the nostril.

An object of the present invention is to provide an applicator and a nasal dispenser device that do not reproduce the above-mentioned drawbacks.

More particularly, an object of the present invention is to provide a nasal applicator that makes it possible, on actuating the device, to dispense the substance into that zone of the nasal fossa in which the substance is assimilated most effectively.

An object of the present invention is also to provide such a nasal dispenser device that does not suffer from the drawbacks of sloping or curved pushers.

An object of the present invention is also to provide a nasal dispenser device of the above-mentioned type that is simple and low-cost to manufacture and to assemble. This applies particularly in certain particular uses in which the nasal dispenser device is designed to expel only a very small number of doses of substance.

An object of the present invention is also to provide such a nasal dispenser device that is simple and reliable for any user to use.

The present invention thus provides a nasal applicator suitable for co-operating with a head of a nasal dispenser device for dispensing a fluid or powder substance into the nose, said head being designed to be inserted at least in part into a nostril when the device is actuated, said nasal applicator being characterized in that said applicator co-operates with the end of the head, said applicator being provided with a bearing piece that extends substantially transversely to the direction in which the substance is dispensed, said bearing piece being suitable for coming to bear under the nostril against the top lip of the user so as to define an insertion angle at which said head is inserted into the nostril.

In an advantageous embodiment of the invention, said applicator includes a ring that can fitted around the end of the head, said bearing piece being connected to said ring.

Advantageously, said applicator includes a hollow cylinder designed to be fitted around said end of the head, said bearing piece being connected to one end of said cylinder.

Preferably, the length of said cylinder determines the depth to which the head penetrates into the nostril, said bearing piece forming an abutment under the nostril to, prevent said head from penetrating any deeper.

In a first variant of the present invention, said bearing piece on said applicator is implemented in the form of a substantially rectangular thin plate having an edge which has a profile suitable for bearing against the top lip of the user.

In a second variant embodiment, said bearing piece of said applicator is implemented substantially in the form of a disk having an edge portion that has a profile suitable for bearing against the top lip, and an opposite edge portion having a profile suitable for bearing against the nose of the user.

The present invention also provides a nasal dispenser device for dispensing a fluid or powder substance into the nose, said device including a dispenser member on which a head provided with a dispenser orifice is mounted, the end of said head being designed to be inserted at least in part in a nostril when the device is actuated, said device being characterized in that it includes an applicator according to any one of claims.

Advantageously, said head includes a cylindrical end provided with the dispenser orifice, said applicator including a hollow cylinder fitted around said cylindrical end of the head by being engaged to an abutment shoulder disposed such that the end of said cylinder is situated substantially at said dispenser orifice.

In a variant embodiment of the present invention, said applicator is an integral part of or is fixed to said head.

In another variant embodiment of the present invention, said applicator is separate and is mounted on said head.

Preferably, said applicator and/or said head is/are provided with means for determining the angular position of said applicator relative to said head.

Other characteristics and advantages of the present invention appear from the following detailed description of various variant embodiments given by way of non-limiting example and with reference to the accompanying drawings, in which:

FIG. 1 is a diagrammatic perspective view showing a head and an applicator of a particular embodiment of the invention; and FIGS. 2 to 5 are diagrammatic perspective views of various variant embodiments of the applicator of the present invention.

As shown in FIGS. 1 to 5, the nasal dispenser device includes a head 100 (or pusher) mounted on a dispenser member (not shown), such as a pump or a valve, said dispenser member itself being mounted conventionally on a container (not shown either) containing the substance. The present invention is applicable to all nasal dispenser devices, and only those portions of the device which are involved in the present invention are shown in the drawings and described below.

In the invention, an applicator 200 is organized to co-operate with the end 110 of the head 100 of the nasal dispenser device, at least a portion of said head being designed to be inserted into the nostril when actuating the device.

All of the variant embodiments shown in the figures have an applicator 200 that is separate from the head 100 and that is organized to be mounted on said head prior to using the device. However, it should be clear that these variants correspond to a preferred embodiment of the invention. The invention also relates to such an applicator that is an integral part of the head, the head and the applicator may then either be integrally molded, or else be fixed together during assembly of the dispenser device.

Similarly, when the nasal applicator is separate, it may be fitted to the head either in removable manner or in fixed manner. A separate applicator is therefore not necessarily a removable applicator.

In the invention, said applicator 200 is provided with a bearing piece 201 which extends substantially transversely to the direction in which the substance is dispensed when said applicator is disposed on the dispenser head 100 of the device. More particularly, in the example shown in FIG. 1, the bearing piece 201 extends perpendicularly to the longitudinal main axis of the head 100, which main axis passes through the dispenser orifice 111.

Advantageously, said applicator 200 is designed to be engaged so as to be fitted around the end 110 of the head 100. In which case said head 100 is advantageously provided with an abutment shoulder 115 which limits the engagement of said applicator 200. In a variant, in particular when the head is conical in shape, the abutment shoulder 115 is unnecessary, the engagement of the applicator being stopped automatically by the increase in the outside diameter of said head 100.

Advantageously, suitable means (not shown) are provided to predetermine the angular position of the applicator 200 relative to said head when they are fitted together, said means being located either on the head 100, or on the applicator 200, or on both of them. These angular positioning means may be provided in the form of flats or of grooves, or in the form of any suitable means.

Figure 3:
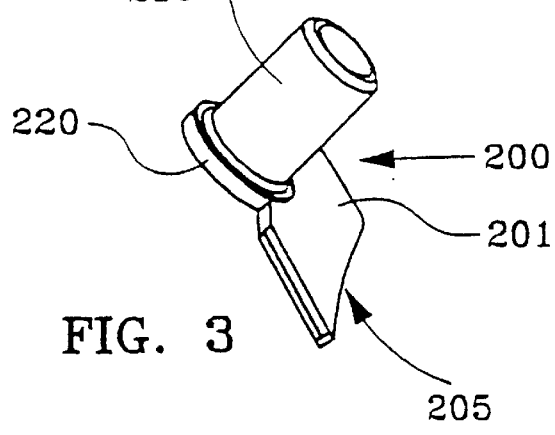
Figure 4:
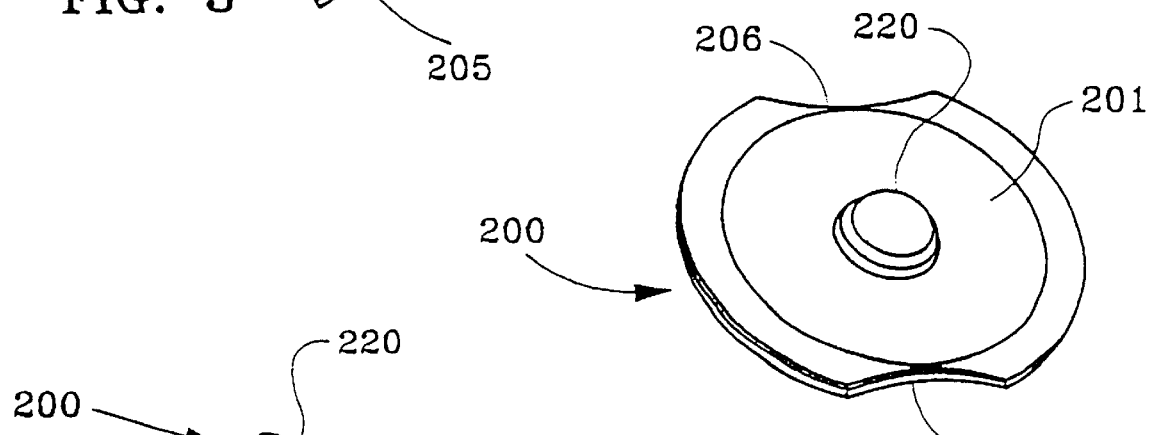
Figure 5:
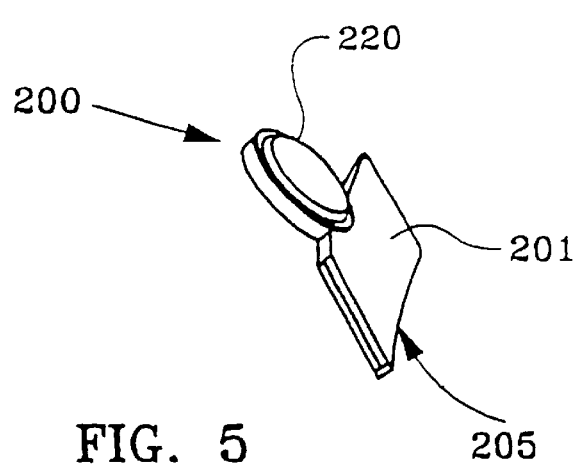

FIGS. 2 to 5 show various embodiments of the applicator 200. Thus, as shown in FIGS. 4 and 5, the applicator is provided with a ring 220 that can be fitted around the end 110 of the dispenser head 100, said bearing piece 201 being connected to said ring 220. In the examples shown in FIGS. 2 and 3, said ring 220 is extended by a hollow cylinder 210 designed to be fitted around said end 110 of the dispenser head 100, the length of said hollow cylinder advantageously determining the depth to which the head 100 penetrates into the nostril. The bearing piece 201 advantageously forms an abutment under the nostril to prevent the head from penetrating any deeper.

In the variants shown in FIGS. 3 and 5, the bearing piece 201 on the applicator 200 is implemented in the form of a thin plate that is advantageously substantially rectangular, and that comes to bear against the top lip of the user. For this purpose, the bearing piece 201 is preferably provided with an edge 205 having a profile matching the shape of the top lip. In the examples shown in FIGS. 1, 2, and 4, said bearing piece is implemented in the general shape of a disk 201. In which case, one edge portion 205 of said disk comes to bear against the top lip and an opposite edge portion 206 comes to bear against the nose of the user. Similarly, said edge portion 205 and/or said opposite edge portion 206 may be of profile matching firstly the top lip and secondly the shape of the nose.

Other variant embodiments are conceivable for performing the function claimed by the present invention.

The device thus operates as follows.

If the applicator 200 is made separate from the dispenser head 100, the user pre-fits said applicator 200 to the end 110 of the head 100. The nasal dispenser device thus includes a radially-projecting portion formed by said bearing piece 201. The user then inserts the head 100, or at least the end 110 of said head, into the nostril. During this operation, the bearing piece 201 of the applicator 200 comes to bear against the top lip, thereby obliging the user to pivot the dispenser device substantially into a horizontal position so that it can be inserted into the nostril. Therefore, the user is strongly encouraged to insert the dispenser head in a direction close the horizontal. Depending on the embodiment of the applicator that is used, the bearing piece 201 comes into abutment either against the top lip only, or else both against the top lip and against the flank of the nose, so as to define firstly the insertion direction in which the head is inserted into the nostril, and secondly the insertion depth to which said head 100 is inserted into the nostril. The user then actuates the device and the dose of substance is dispensed in the desired zone, namely at the inferior turbinate bone of the nostril.

A particular advantage of the invention is that it makes is possible for the substance to be dispensed effectively while limiting the manufacturing costs of the device. The applicator of the invention is very easy to mold and it fits onto a dispenser head that does not need to be sloping. The manufacturing complications caused by such sloping heads are thus avoided.

The device of the present invention also offers the following additional advantages:

the nasal dispenser device of the present invention is easy to adapt to be suitable either for child use or for adult use; for this purpose, it is necessary merely to vary the length of the cylinder 210 of the applicator 200 so that the length of said cylinder is chosen to correspond to the optimal distance to which it should be inserted into the nostril, depending on whether the user is a child or an adult; and when the applicator 200 is engaged so as to be fitted around the end 110 of the head 100, and the applicator 200 is provided with a hollow cylinder 210, the end 210 of the head may be implemented cylindrically. This makes it possible to simplify molding of the top portion of the nasal pusher, in particular at the dispenser orifice 111. In the example shown in FIG. 1, that portion of the head in which the external wall of the head is connected to its internal structure (in which, in particular, the internal nozzle is fixed) may be offset away from the dispenser orifice, i.e. it may be situated at the abutment shoulder 115. Thus, molding defects at this junction do not adversely affect the spraying of the substance, which takes place at the dispenser orifice.

The present invention thus makes it possible to provide a nasal dispenser device that is simple, low-cost to manufacture (in particular to mold) and to assemble. This device is further simple and reliable for anyone to use, the bearing piece 201 on the applicator encouraging or even obliging the user to insert the head of the apparatus into the nostril in the desired direction so as to dispense the dose of substance into the desired zone of the nostril. This is particularly advantageous in the field of pharmacy in which the measuring out of the substance must be very accurate and its effectiveness optimized because of the often high cost of the substances to be dispensed.

What is claimed is:

1. A nasal applicator in combination with a head (100) of a nasal dispenser device for dispensing a substance into a user's nose, the combination comprising:

said head (100) including a pressure handle that is pushable by the user to actuate the device, said head being insertable at least in part into a nostril of the nose when the device is actuated; and said nasal applicator including
(a) a portion mounted onto an end (110) of said head (100), and
(b) a bearing piece (201) that extends from said portion substantially transversely to a direction in which the substance is dispensed, said bearing piece being spaced apart from said pressure handle;

wherein said bearing piece (201) is constructed to bear under the nostril against a top lip of the user so as to define an insertion angle at which said head (100) is inserted into the nostril.

2. A combination according to claim 1, wherein said portion is a ring (220) that is fittable around said end (110) of said head (100), and said bearing piece (201) is connected to said ring (220).

3. A combination according to claim 1, in which said portion is a hollow cylinder (210) that is fittable around said end (110) of said head (100), and said bearing piece (201) is connected to one end of said hollow cylinder (210).

4. A combination according to claim 3, in which the length of said hollow cylinder (210) determines a depth to which said head (100) penetrates into the nostril, and said bearing piece (201) forms an abutment under the nostril to prevent said head from penetrating beyond said depth.

5. A combination according to claim 1, in which said bearing piece (201) is a substantially rectangular thin plate having and edge (205) which has a profile suitable for bearing against the top lip of the user.

6. A combination according to claim 1, in which said bearing piece (201) is a disk having (1) an edge portion (205) that has a profile suitable for bearing against the top lip, and (2) an opposite edge portion (206) having a profile suitable for bearing against the nose of the user.

7. A combination according to claim 1, further including a dispenser member on which said head (100) is mounted, said head provided with a dispenser orifice (111).

8. A combination according to claim 7, in which said end (110) of said head (100) has a cylindrical shape, said end is provided with said dispenser orifice (111), said portion (210) of said nasal applicator (200) has a cylindrical shape and is fitted around said end (110) of said head by being engaged to an abutment shoulder (115) disposed such that said portion (210) is situated substantially at said dispenser orifice (111).

9. A combination according to claim 7, in which said nasal applicator (200) is one of an integral part of said head and fixed to said head (100).

10. A combination according to claim 7, in which said nasal applicator (200) is separatable from said head (100).

11. A combination according to claim 7, in which one of said nasal applicator (200) and said head (100) is provided with means for determining an angular position of said nasal applicator (200) relative to said head (100).

* * * * *